United States Patent [19]

Allen et al.

[11] Patent Number: 5,672,161
[45] Date of Patent: Sep. 30, 1997

[54] NEEDLE ASSEMBLY HAVING SINGLE-HANDEDLY ACTIVATED NEEDLE BARRIER

[75] Inventors: William J. Allen, Stratford; Jeffrey A. Stein, Woodbridge, both of Conn.

[73] Assignee: Becton, Dickinson and Company, Franklin Lakes, N.J.

[21] Appl. No.: 717,384

[22] Filed: Sep. 20, 1996

[51] Int. Cl.$^6$ .................................................. A61M 5/32
[52] U.S. Cl. .................................................. 604/263; 604/192
[58] Field of Search .................................................. 604/263, 192, 604/187, 110, 198

[56] References Cited

U.S. PATENT DOCUMENTS

| | | | |
|---|---|---|---|
| 2,559,474 | 7/1951 | Son | 128/215 |
| 2,739,591 | 3/1956 | Yochem | 128/218 |
| 4,573,976 | 3/1986 | Sampson et al. | 604/198 |
| 4,738,663 | 4/1988 | Bogan | 604/198 |
| 4,790,828 | 12/1988 | Dombrowski et al. | 604/198 |
| 4,892,521 | 1/1990 | Laico et al. | 604/192 |
| 4,915,696 | 4/1990 | Feimer | 604/192 |
| 4,976,699 | 12/1990 | Gold | 604/192 |
| 4,994,046 | 2/1991 | Wesson et al. | 604/198 |
| 5,026,356 | 6/1991 | Smith | 604/192 |
| 5,188,611 | 2/1993 | Orgain | 604/192 |
| 5,215,534 | 6/1993 | De Harde et al. | 604/198 |
| 5,232,455 | 8/1993 | Hollister | 604/263 |
| 5,348,544 | 9/1994 | Sweeney et al. | 604/192 |
| 5,466,223 | 11/1995 | Bressler et al. | 604/110 |
| 5,509,907 | 4/1996 | Bevilacqua | 604/263 |

*Primary Examiner*—John D. Yasko
*Attorney, Agent, or Firm*—John L. Voellmicke

[57] ABSTRACT

A needle assembly having a single-handedly activated needle barrier includes a needle cannula having a lumen therethrough. A needle hub having an interior cavity terminating at an open proximal end of the hub is connected to the needle cannula so that the lumen is in fluid communication with the interior cavity. A guide element having a retaining groove therethrough is connected to the needle hub. An elongate barrier arm having a proximal end and a distal end includes a barrier element at its distal end. The barrier element includes a proximal end and a needle passageway therethrough. The barrier arm is positioned within the groove of the guide element and the needle cannula is positioned at least partially within the barrier element. The barrier arm is movable from at least a first retracted position wherein the distal end of the cannula passes through the barrier element so that the distal end of the needle cannula is exposed, to a second extended position wherein the barrier element surrounds the distal end of the needle cannula to help prevent accidental contact with the distal end of the needle cannula. Locking structure to prevent movement of the barrier arm from the second extended position is activated by movement of the barrier arm into the second extended position.

20 Claims, 9 Drawing Sheets

NEEDLE ASSEMBLY HAVING SINGLE-HANDEDLY ACTIVATED NEEDLE BARRIER

1. FIELD OF THE INVENTION

The subject invention relates to safety needle barriers, capable of single-handed activation, for hypodermic needles, blood collection needles, catheter needles and other medical implements for helping to prevent accidental needle sticks.

2. DESCRIPTION OF THE PRIOR ART

Accidental sticks with a used needle cannula can transmit disease. As a result, the prior art teaches many needle assemblies and medical devices having safety shields which can be positioned to prevent accidental contact with the needle point after use of the medical device. Some prior art safety shields define a rigid cylinder which can be telescoped in a proximal direction over a used needle cannula. These devices are effective, however, they require a two-handed procedure wherein the healthcare worker holds the medical instrument with one hand and manually advances the needle shield with the other hand. Needle shields of this type, which fit over syringe barrels, are also expensive because each separate size syringe barrel must have its appropriately sized shield.

In addition to needle shielding devices which require two-handed operation, the prior art also teaches needle shielding devices which are automatic and do not require one-handed or two-handed activation. These needle shield assemblies also have important deficiencies. Most notably, the shield can be activated unintentionally thus rendering the unused instrument unsuitable for its intended purpose. Also many procedures wherein needles and hypodermic syringes are used the needle is first used to pierce a vial stopper to draw medication into the syringe and then used to inject the medication into the patient. However, automatically activatable needle shields can be activated during the filling operation and render the medication undeliverable. Some automatic safety shields, in their initial position, cover the tip of the needle making it difficult for the healthcare worker to see precisely where the needle will be placed in the patient and/or the depth of penetration of the needle into the patient. This is particularly problematical where the needle is being used to draw blood or to enter a vein for the purpose of delivering medication. Also, some of the automatic devices which initially cover the needle tip make the needle look like it is safely protected when the shield will provide little or no resistance to incidental contact. Even in its uncontaminated state, a hypodermic needle can be an instrument to provide a painful puncture wound to an unsuspecting user.

Although the prior art teaches many needle shielding structures there is still a need for a simple, straight-forward, reliable, easily fabricated needle assembly which is self-contained, capable of single-handed activation, and can be used with a variety of medical instruments.

SUMMARY OF THE INVENTION

The subject invention is directed to a needle assembly having a single-handedly activated needle barrier. The needle assembly includes a needle cannula having a proximal end, a distal end and a lumen therethrough defining a longitudinal axis. A needle hub having an interior cavity terminating at an open proximal end of the hub is connected to the needle cannula so that the lumen is in fluid communication with the interior cavity. A guide element having a retaining groove therethrough is connected to the needle hub. An elongate barrier arm having a proximal end and a distal end includes a barrier element at its distal end. The barrier element includes a proximal end and a needle passageway therethrough having a longitudinal axis. The barrier arm is positioned within the groove of the guide element and the needle cannula is positioned at least partially within the barrier element. The barrier arm is movable from at least a first retracted position wherein the distal end of the cannula passes completely through the barrier element so that the distal end of the needle cannula is exposed, to a second extended position wherein the barrier element surrounds the distal end of the needle cannula to prevent accidental contact with the distal end of the needle cannula. Locking structure is provided to prevent movement of the barrier arm from the second extended position. The locking structure is activated by movement of the barrier arm into the second extended position. A finger contact surface on the barrier is provided for applying digital pressure to the barrier arm to move the barrier arm into the second extended position.

DETAILED DESCRIPTION

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1–12 a needle assembly 20 having a single-handedly activated needle barrier includes a needle cannula 21 having a proximal end 22, a distal end 23 and a lumen therethrough. Distal end 23 includes sharpened distal tip 25. A needle hub 27 having an interior cavity 28, which terminates at an open proximal end 29 of the hub, is connected to the proximal end of needle cannula 21 so that the lumen is in fluid communication with the interior cavity of the hub. In this preferred embodiment, interior cavity 28 is frusto-conically shaped.

Figures 13, 14:
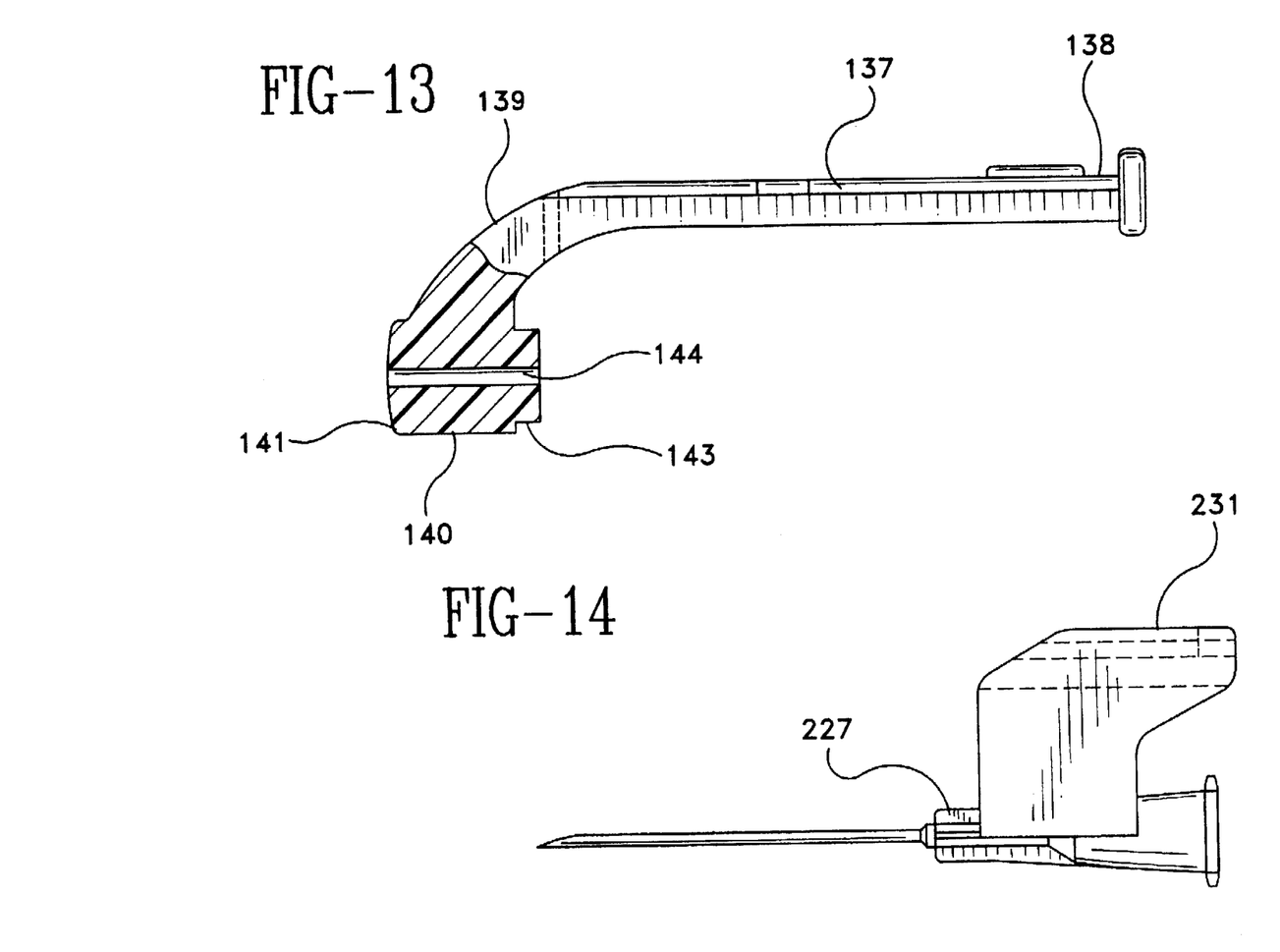
FIG. 13 is a partial cross-sectional side elevation view of an alternative barrier arm of the present invention.
FIG. 14 is an alternative embodiment of the needle assembly of FIGS. 1–12 wherein the needle hub and guide element are integrally formed.

A guide element 31 is connected to the needle hub and includes a retaining groove 32. In this embodiment, the guide element is attached to the needle hub through the use of any suitable joining technique such as adhesives, ultrasonic welding and the like. For low volume production attaching the guide element to an existing hub is desirable from a cost standpoint. It is within the purview of the present invention to include an integrally molded one-piece hub and guide element. For high volume production it may be desirable that the needle hub and guide element be of one-piece integrally molded thermoplastic, as illustrated in FIG. 14. The retaining groove in the guide element is generally axially oriented and dimensioned to accept an elongate barrier arm 37, as will be described in more detail hereinafter. The elongate barrier arm includes a proximal end 38 and a distal end 39. The distal end of the barrier arm includes barrier element 40 having a distal end 41, a proximal end 43 and a needle passageway 44 therethrough. The elongate barrier arm, including the barrier element, is preferably integrally molded of the same material. However, the barrier element and the barrier arm can be separately formed and joined together by any suitable means such as adhesive, ultrasonic welding and frictional or snap-fit type engagement. The barrier arm and barrier element can also be separately formed and connected by a separate element such as a metal clip. The barrier arm is positioned within retaining groove 32 of guide element 31, and needle cannula 21 is positioned within needle passageway 44 of the barrier element 40. The retaining groove guide element 31 is dimensioned and oriented to accept the elongate barrier arm.

Figure 1:
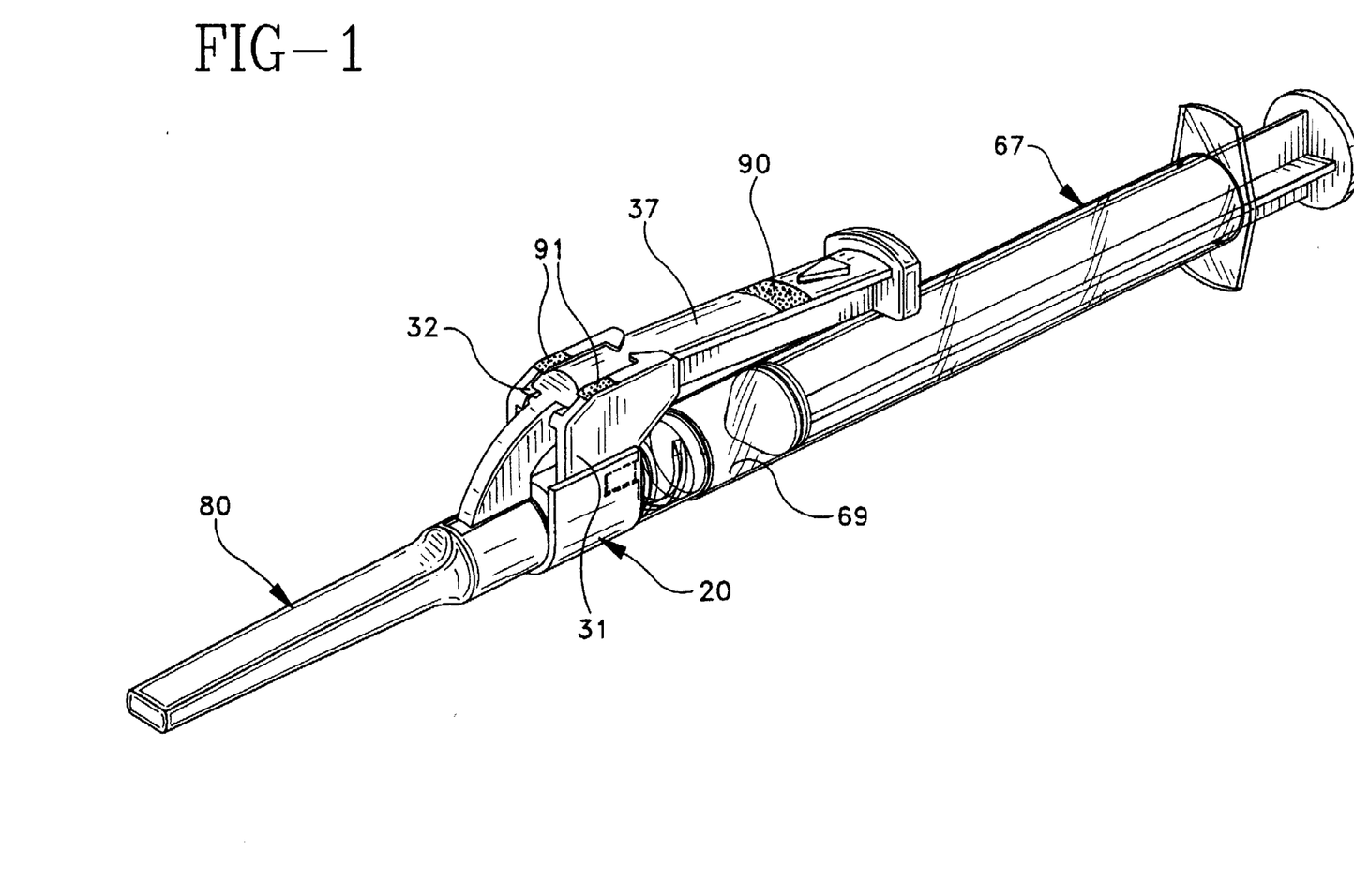
FIG. 1 is a perspective view of the needle assembly having a single-handedly activatable needle barrier, attached to a hypodermic syringe.
Figure 2:
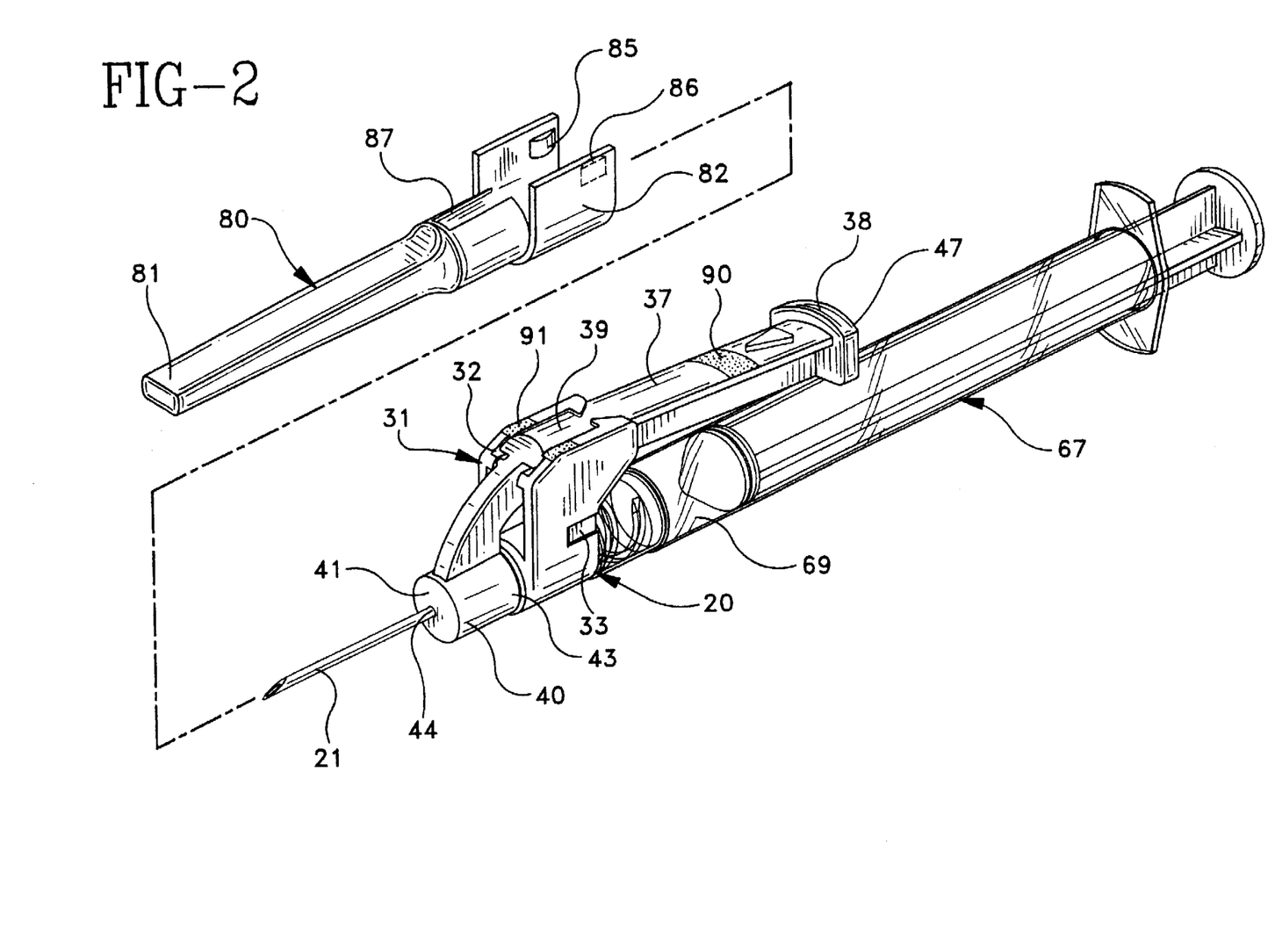
FIG. 2 is an exploded perspective view of the needle assembly of FIG. 1 with the needle shield removed.
Figure 3:
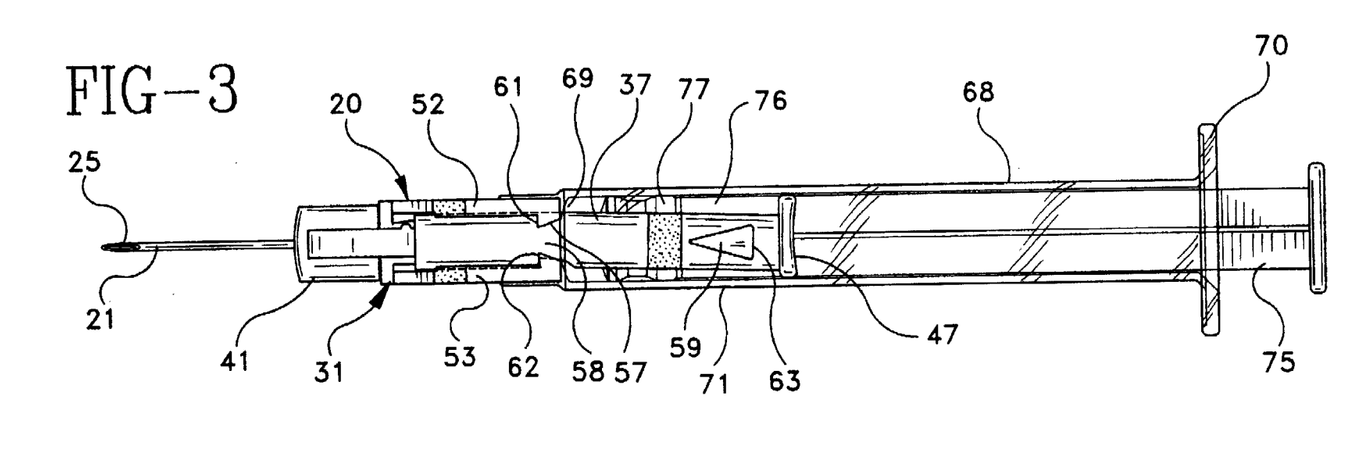
FIG. 3 is a top plan view of the needle shield assembly of FIG. 2 illustrating the barrier arm in the retracted position.
Figure 4:
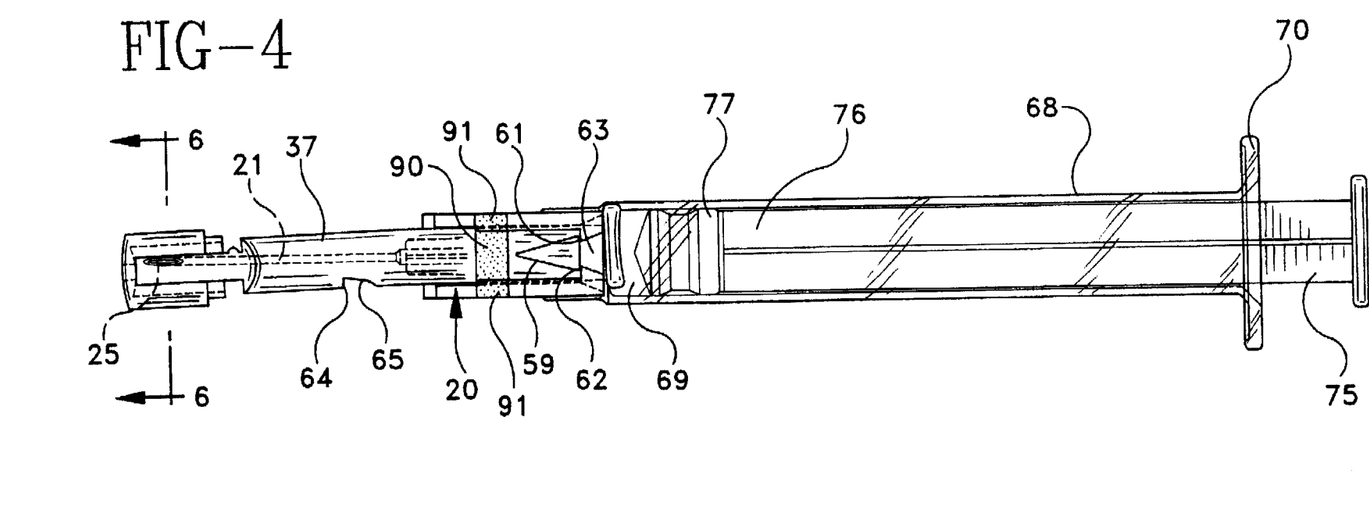
FIG. 4 is a top plan view of the needle assembly of FIG. 2 illustrating the barrier element in the extended position.
Figure 5:
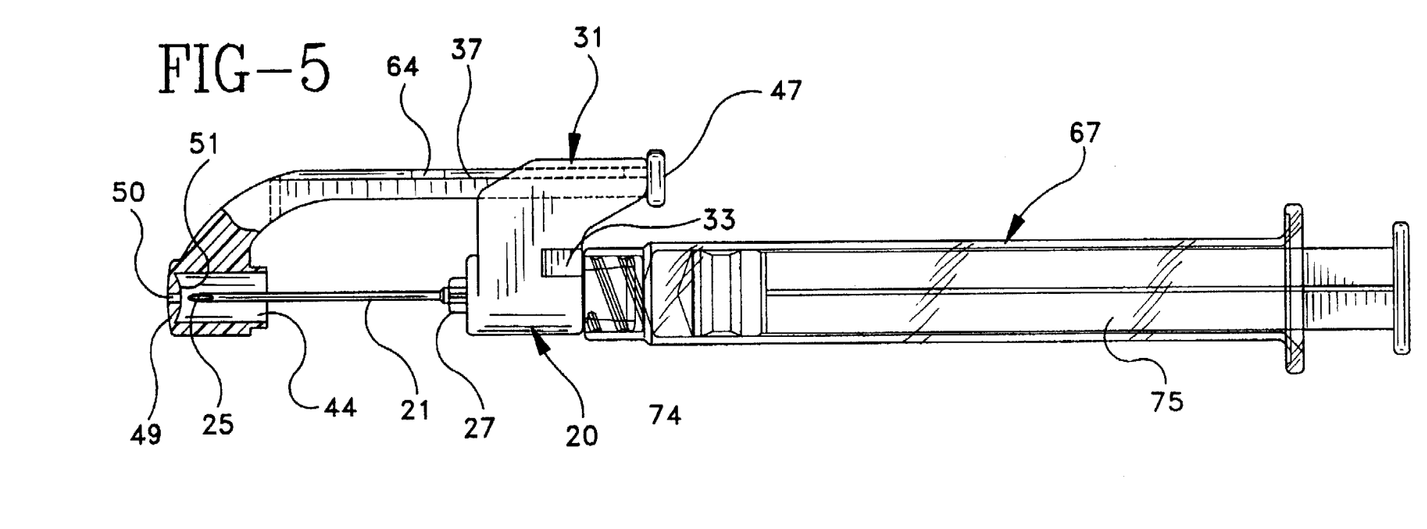
FIG. 5 is a partially cross-sectional side elevation view of the needle assembly of FIG. 4.

Elongate barrier arm 37 is movable from at least a first retracted position as illustrated in FIGS. 2 and 3, wherein distal end 23 of the needle cannula passes completely through the barrier element so that the distal end of the needle cannula is exposed, to a second position, as illustrated in FIGS. 4 and 5, wherein the barrier element surrounds distal end 23 and sharpened distal tip 25 of the needle cannula to prevent accidental contact with the distal end of the needle cannula.

The barrier arm includes a finger contact surface to allow the single-handed movement of the barrier arm from the first retracted position of FIGS. 2 and 3 to the second extended position of FIGS. 5 and 5. In this preferred embodiment, finger contact surface 47 is provided on the proximal end of the elongate barrier arm. This position for the finger contact surface is preferred because it is the farthest position from the sharp needle tip. The barrier arm can be single-handedly advanced from the first retracted position to the second extended position by holding the syringe in one hand and pushing on finger contact surface 47 with the thumb or the index finger of the holding hand. The ability to allow single-handed operation is an important feature of the present invention since it allows the person administering the injection to use the other hand for other purposes such as applying pressure to a vein to prevent bleeding.

An advantage of the present invention is that one needle assembly can be sized so that it can be used with several different sizes of syringes, for example syringes having 3 ml and 5 ml volume capacities.

Figure 6:
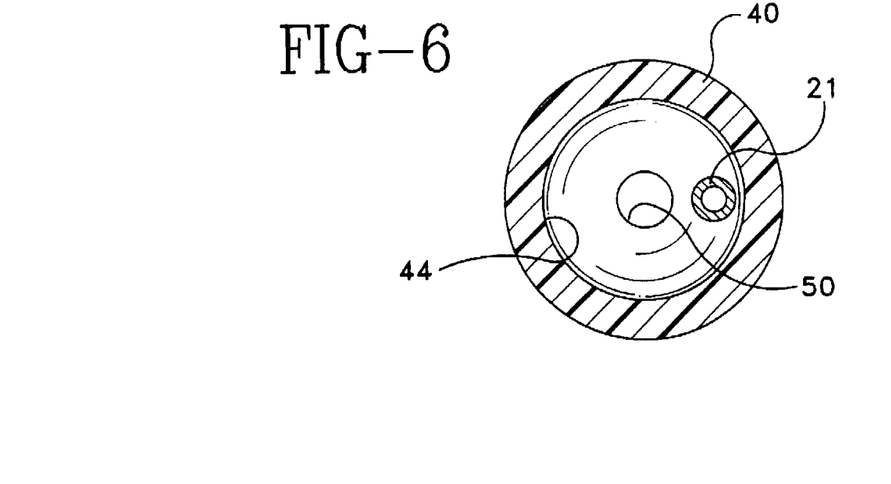
FIG. 6 is a cross-sectional view of the needle assembly of FIG. 4 taken along line 6—6.
Figure 7:
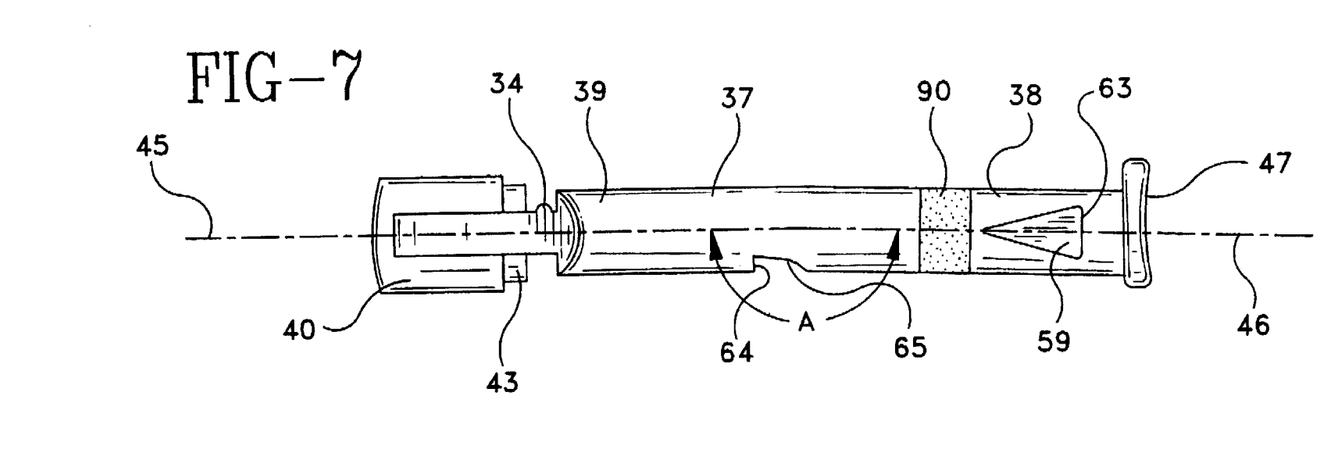
FIG. 7 is a top plan view of the barrier arm of the needle assembly of the present invention.
Figure 8:
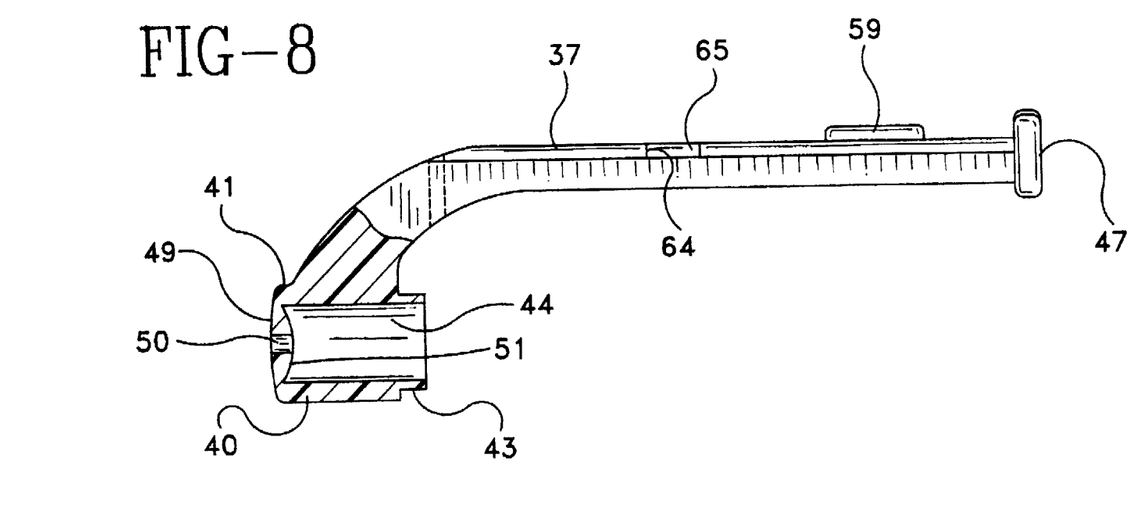
FIG. 8 is a partially cross-sectional side elevation view of the barrier arm of FIG. 7.
Figure 9:
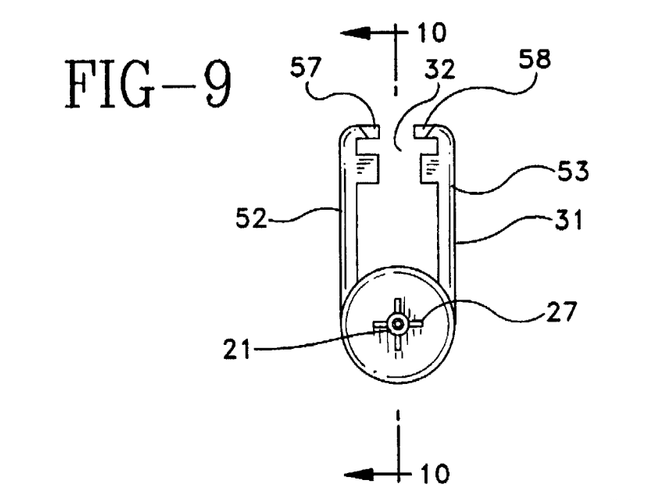
FIG. 9 is a side elevational end view of the assembly of the needle cannula, needle hub and guide element of the present invention.
Figure 10:
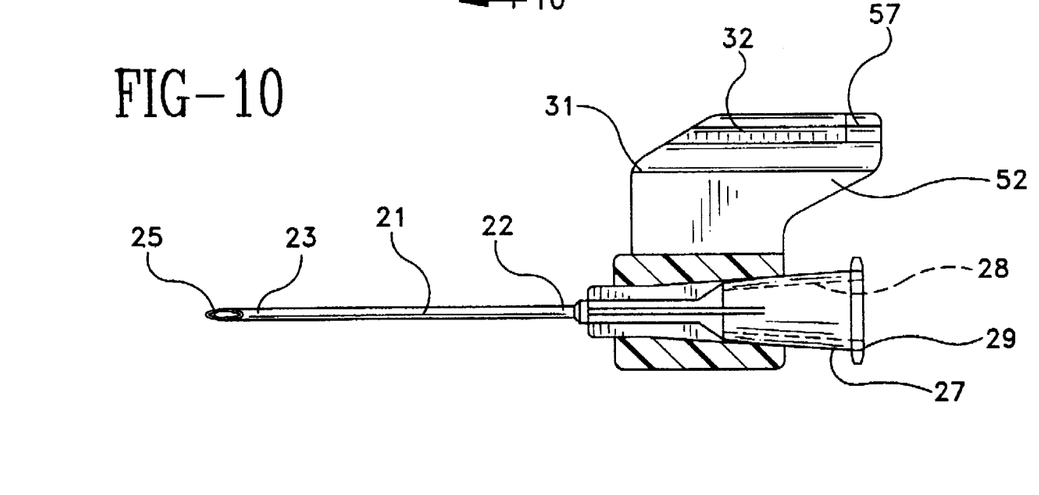
FIG. 10 is a partial cross-sectional view of the assembly of FIG. 9 taken along line 10—10.
Figure 11:
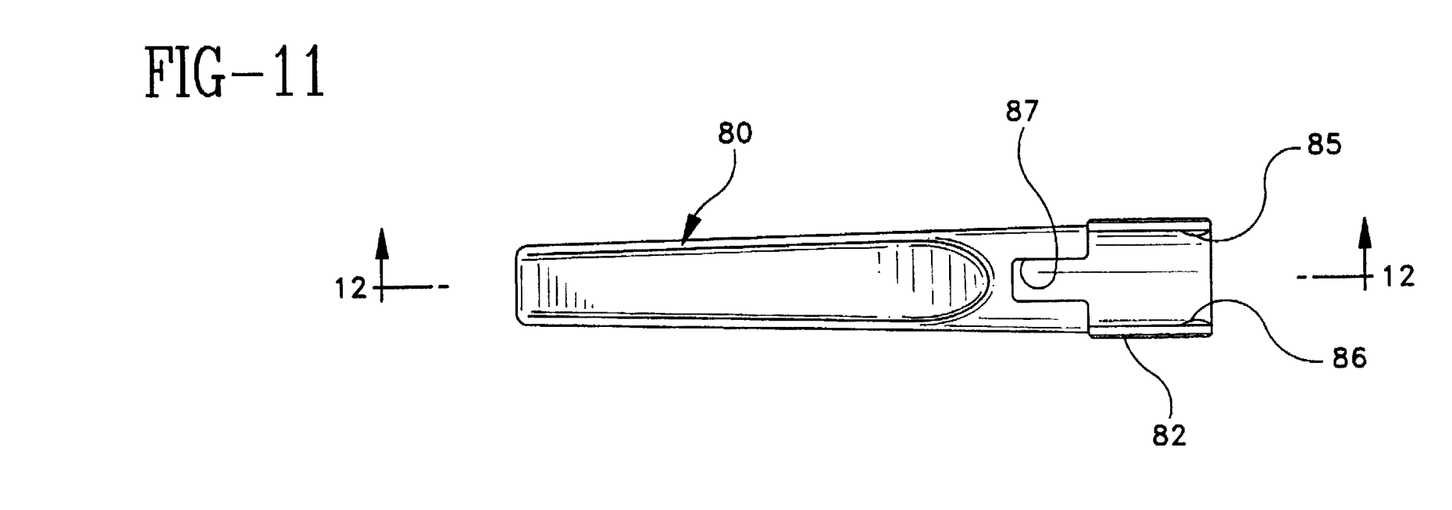
FIG. 11 is a top plan view of the needle shield of the present invention.
Figure 12:
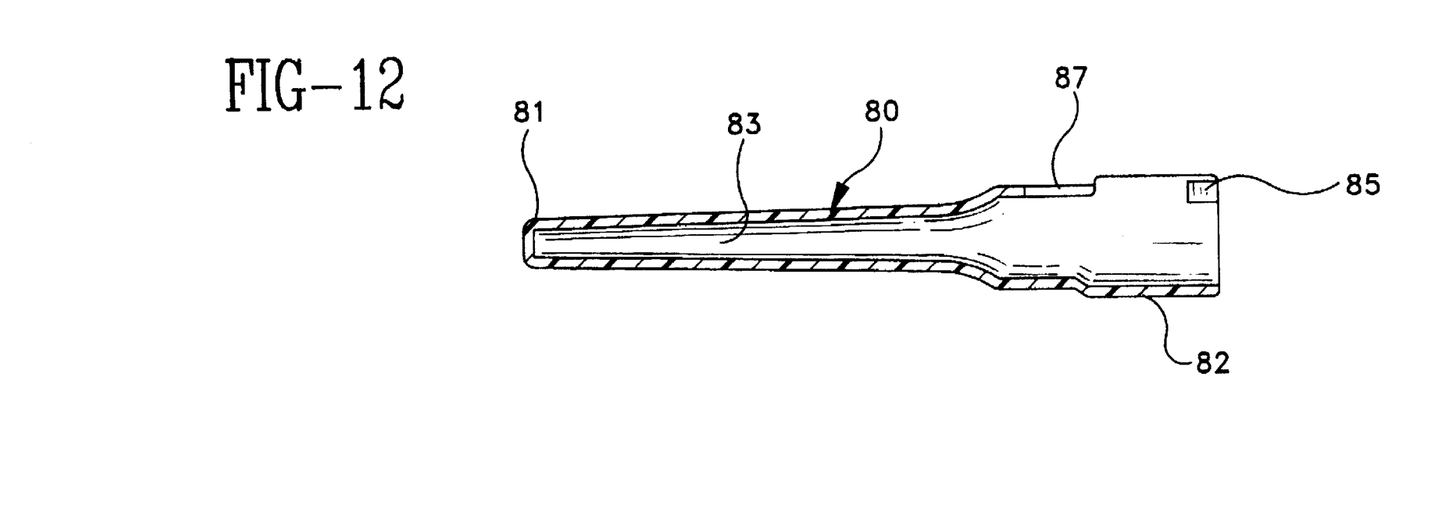
FIG. 12 is a cross-sectional view of the needle shield of FIG. 11 taken along line 12—12.

An important feature of the present invention includes locking means for preventing movement of the barrier arm from the second extended position wherein the locking means is activated by movement of the barrier arm into the second extended position. In this preferred embodiment, the barrier element further includes barrier wall 49 at distal end 41 of the barrier element. Barrier wall 49 includes barrier wall aperture 50, which is part of needle passageway 44, but having a reduced diameter which is larger than the needle cannula diameter and smaller than the passageway diameter thus forming annular ledge 51. In the preferred embodiment, locking means includes the distal end of the barrier arm defining a distal longitudinal axis 45 and the proximal end of the barrier arm defining a proximal longitudinal axis 46. The barrier arm is configured so that the distal longitudinal axis and the proximal longitudinal axis are at obtuse angle A with respect to each other so that when the barrier arm is in the second extended position the distal end of the needle cannula is positioned proximally of barrier wall 49 and out of alignment with barrier wall aperture 50 as best illustrated in FIGS. 4 and 6. Because distal end 23 of the needle cannula is out of alignment with barrier wall aperture 50 any attempt to move the barrier arm from the second extended position will cause the sharpened distal tip 25 end of the needle cannula to embed itself into the annular ledge portion 51 of the barrier wall to help prevent re-exposing the distal end of the needle cannula. This is an important feature of the present invention because the locking means is accomplished without any additional parts and structures such as latches, ledges, triggers and the like which add to cost and complexity and can adversely affect reliability. The simplicity of the present invention is dramatized by the fact that a needle assembly usually consists of two components, a hub and a needle, while the present invention provides a complete needle assembly having a single-handedly activatable needle barrier with only four components, a needle cannula, a hub, a guide element and elongate barrier arm. If the guide element and needle hub are integrally molded, the present invention consists of only three components.

Although it is not necessary to practice the present invention, it is preferable to have a second, redundant, component to the locking means to further resist motion of the barrier arm from the second extended position to the first retracted position. This component of the locking means is accomplished without additional components and by configuring the guide element and the barrier arm with various combinations of projections and recesses which will allow the barrier arm to be forced through the guide element, in a distal direction, by application of digital pressure on finger contacting surface 47. However, the projections and recesses are configured such that returning the barrier arm to the first retracted position is not possible using forces normally associated with operation the invention. In this embodiment, the locking means further includes sidewalls 52 and 53 of the guide element having projections 57 and 58 respectively, configured to interact with a raised projection 59 on barrier arm 37. Raised projection 59 is wedge-shaped and larger at its proximal end than at its distal end. When force is applied to the barrier arm to move the barrier arm from the first retracted position to the second extended position, distal motion of the barrier arm will cause raised projection 59 to contact projections 57 and 58 on the guide element. Additional force will be required to force the raised projection past the guide element projections. Once this occurs, the projections will snap back to their original position and ledge 61 on projection 57, and ledge 62 on projection 58 will form a locking relationship with respect to back wall 63 of raised projection 59 to prevent movement, as illustrated in FIG. 4, will help prevent movement of the barrier arm proximally from the second extended position.

In the preferred embodiment the projections 57 and 58 on the guide element and raised projection 59 on the barrier arm are configured so that when the barrier arm is moved distally into the second extended position, the projections 52 and 53 will snap past the end of raised projection 59 making an audible sound to provide an audible indication that the barrier arm is moved into the second extended position. It is preferred that two projections be provided on the guide element, however, only one projection will work and is in the purview of the present invention.

The preferred embodiment also includes means for visually determining that the barrier arm 37 is in the second extended position which includes color segment 90 on barrier arm 37 and at least one color segment on the guide element. In this embodiment, there are two color segments 91 on guide element 31. When the barrier arm is in the second extended position color segment 90 and color segments 91 will align, as best illustrated in FIG. 4, to form a continuous transverse color band. Any color, including black and white, can be used to form the color segments. However, green is preferred because it is generally accepted to indicate safety. Accordingly, when the green color segments are precisely aligned the needle assembly of the present invention is safely locked with the barrier arm in the second extended position.

The present invention also preferably includes structure for releasably holding the barrier arm in the first retracted position. This function can be accomplished by dimensioning the barrier arm and the retaining groove in the guide element to have a frictional fit. In this preferred embodiment, where the distal end and the proximal end of the barrier arm define longitudinal axes which are at an obtuse angle with respect to each other, the non-straight configuration of the barrier arm when it enters a groove sized for a straight barrier arm will provide the frictional relationship to keep the barrier arm from moving distally under less than the desired force. Further, a recess 64 is provided in the barrier arm for accepting projection 58 on the guide element when the barrier arm is in the retracted position. At this position, the barrier arm does not have to be tightly contained within the retaining groove. Accordingly, the plastic components are not stressed during the long period of time between manufacture and use. Upon applying force to the barrier arm to move it distally, projection 58 rides up incline portion 65 of recess 64 to immediately increase the force necessary to move the barrier arm in a distal direction. This structure designed to increase the force retains the barrier arm in the retracted position. The shapes of projection 58 and incline portion 65 can also be configured so that there is an audible click when projection 58 leaves recess 64, further communicating to the healthcare worker that the barrier arm is in motion toward the second extended position. The barrier arm can also be releasably held in the first retracted position by the action of a rib 34 on the barrier arm and a projection or recess in the guide element (not shown) which requires additional force to move rib 34 past the projection or recess.

Although the needle assembly of the present invention is suitable for use with a wide variety of medical devices, including blood collection devices, it is illustrated in FIGS. 1–5 as being used with hypodermic syringe 67. Syringe 67 includes a syringe barrel 68 having an elongate cylindrical body defining a chamber 69 for retaining fluid. The barrel includes an open proximal end 70, a distal end 71 and a frusto-conically shaped tip extending from the distal end having a passageway therethrough in fluid communication with the chamber. The frusto-conically shaped tip of the syringe barrel frictionally engages the frusto-conically shaped cavity of the preferred needle hub 27. For the purpose of drawing fluid into and out of chamber 69 the syringe includes an elongate plunger 75 having a distal end 76 which including a stopper 77 which is in fluid-tight slidable engagement with the interior of the chamber.

Figure 15:
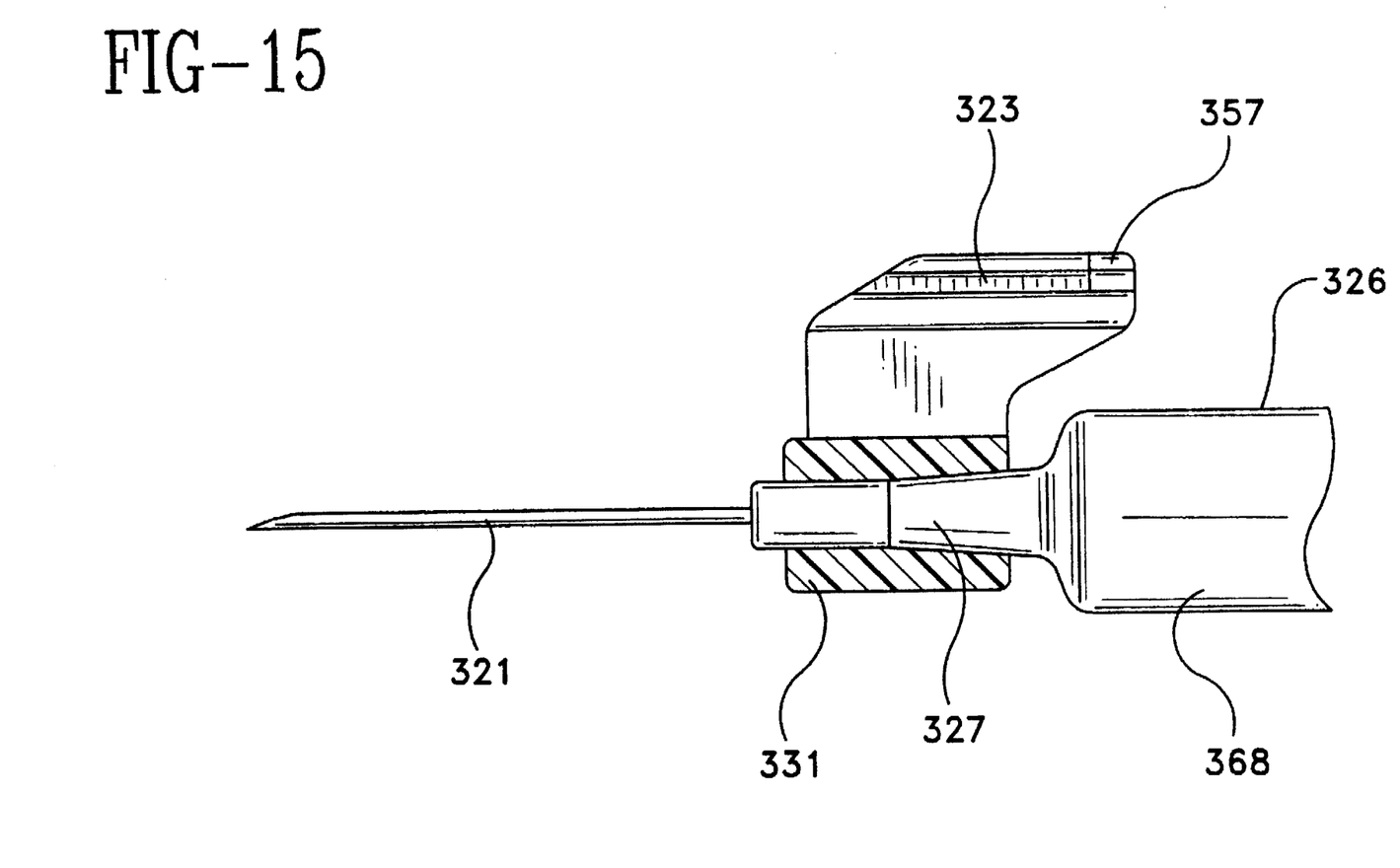
FIG. 15 is another alternate embodiment of the present invention wherein the syringe barrel and the needle hub are integrally formed.

It is within the purview of the present invention to include a needle hub which is integrally molded with a syringe barrel made with thermoplastic or glass material, as illustrated in FIG. 15. In this configuration, the tip of the syringe barrel, which extends from the distal end of the barrel, and the needle hub are one in the same element. In this configuration, the needle is preferably attached to the needle hub/syringe barrel through the use of an adhesive so that the needle cannot be removed from the syringe barrel. This configuration is ideally suited for prefilled syringes which are usually made with a permanently attached needle cannula.

The preferred needle assembly further includes an elongate needle shield 80 having a distal end 81, a proximal end 82 and a cavity 83 therebetween for receiving the needle cannula. The proximal end of the needle shield is configured to releasably engage a portion of the guide element for holding the needle shield in a needle protecting position while the barrier arm is in the first retracted position. The needle shield is configured so that when the barrier arm is in the second extended position, the needle shield cannot be connected to the needle assembly. Needle shield 80 is removably attached to the guide element through action of projections 85 and 86 at the proximal end of the needle shield which interact with complimentary recesses 33 on the guide element. Needle shield 80 further includes proximal top opening which is configured to accept the barrier arm so that there can be a substantially complete shielding of the needle cannula. Accordingly, the needle shield can effectively protect the needle cannula from damage and inadvertent contact from the time of manufacture until the time of use when the shield is appropriately discarded. After the barrier element is moved to the second extended position, the needle shield can no longer be used with the needle assembly of the present invention.

Adverting to FIG. 13, an alternate barrier arm 137 of the present invention includes a proximal end 138, a distal end 139. The barrier arm includes a barrier element 140 having a distal end 141, a proximal end 143 and a needle passageway 144 therethrough. This alternate needle assembly functions in substantially the same manner as the needle assembly taught in FIGS. 1–12 except that the needle passageway 144 is generally continuous throughout the length of the barrier element. When the barrier element is moved to the second extended position, the sharpened tip of the needle cannula will be pressing firmly against the sidewalls of the needle passageway so that any attempt to move the elongate barrier arm 137 from the second extended position to the first retracted position will cause the needle cannula to embed itself in the sidewall of needle passageway 144 to inhibit proximal movement of the barrier arm.

FIG. 14 illustrates an alternative embodiment of the needle shield assembly of the present invention, discussed in more detail herein above, wherein the needle hub 227 and guide element 231 are integrally formed of one-piece construction preferably of thermoplastic material.

FIG. 15 illustrates still another embodiment of the present invention, discussed herein above, wherein needle hub 327 and syringe barrel 368 are integrally formed into a one-piece hub syringe barrel element 326. Needle cannula 321 is permanently attached to the hub syringe barrel element preferably through the use of adhesives such as epoxy. Guide element 321 is attached directly to the hub syringe barrel element 326 either before or after needle cannula 321 is installed.

What is claimed is:

1. A needle assembly having a single-handedly activatable needle barrier comprising:

a needle cannula having a proximal end, a distal end, and a lumen therethrough defining a longitudinal axis;

a needle hub having an interior cavity terminating at an open proximal end of said hub, said hub connected to said needle cannula so that said lumen is in fluid communication with said interior cavity;

a guide element connected to said needle hub having a retaining groove therethrough;

an elongate barrier arm having a proximal end and a distal end, said distal end of said barrier arm including a barrier element having a distal end, a proximal end and a needle passageway therethrough having a longitudinal axis, said barrier arm positioned within said groove of said guide element and said needle cannula positioned at least partially within said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position, said locking means being activated by movement of said barrier arm into said second extended position, said locking means including said distal end of said barrier arm defining a distal longitudinal axis and said proximal end of said barrier arm defining a proximal longitudinal axis, said barrier arm being configured so that said distal longitudinal axis and said proximal longitudinal axis are at an obtuse angle with respect to each other and when said proximal end of said barrier arm is in said groove said needle passageway longitudinal axis is misaligned with said needle cannula longitudinal axis; and finger contact surface on said barrier arm for applying digital pressure to said barrier arm to move said barrier arm into said second extended position.

2. The needle assembly of claim 1 wherein said locking means includes said barrier element having a distal barrier wall with an aperture therethrough, said barrier wall aperture being effectively smaller than said needle passageway.

3. The needle assembly of claim 1 wherein said locking means includes a projection on said barrier arm configured to allow said barrier arm to pass through said groove of said guide element in a distal direction but not in a proximal direction.

4. The needle assembly of claim 3 wherein said projection is wedge-shaped being larger at its proximal end than at its distal end.

5. The needle assembly of claim 1 having means for releasably holding said barrier arm in said first retracted position.

6. The needle assembly of claim 5 wherein said means for releasably holding said barrier arm in said first retracted position includes a projection on said guide element engaging a recess in said barrier arm said projection, and said recess being shaped to hold said barrier arm in said first retracted position and to allow to move said second extended position upon the application of distally directed digital force to said barrier arm.

7. The needle assembly of claim 1 further including an elongate needle shield having a distal end, a proximal end and a cavity therebetween for receiving said needle cannula, said proximal end of said needle shield being configured to releasably engage a portion of said guide element for holding said needle shield in a needle protecting position while said barrier arm is in said first retracted position and said needle shield being incapable of engaging said guide element when said barrier arm is in said second extended position.

8. The needle assembly of claim 1 wherein said guide element is integrally formed with said needle hub in a one-piece structure.

9. The needle assembly of claim 1 wherein said elongate barrier arm integrally formed with said barrier element into a one-piece structure.

10. The needle assembly of claim 1 connected to a syringe barrel having an elongate cylindrical body defining a chamber for retaining fluid, an open proximal end, a distal end and a tip extending from said distal end having a tip passageway therethrough in fluid communication with said chamber, said tip of said syringe barrel being positioned in said cavity of said needle hub.

11. The needle assembly of claim 1 wherein said elongate barrier arm is made of thermoplastic material.

12. The needle assembly of claim 1 wherein the distal end of the needle cannula includes a sharpened distal tip.

13. The needle assembly of claim 1 wherein said needle hub is integrally formed with a syringe barrel having an elongate cylindrical body defining a chamber for retaining fluid, an open proximal end and a distal end, said needle hub being integrally formed with the distal end of said syringe barrel so that said chamber and said lumen of said cannula are in fluid communication.

14. The needle assembly of claim 1 further including means for providing an audible indication when said elongate barrier arm is moved distally into said second extended position.

15. The needle assembly of claim 1 further including means for visually indicating that said elongate barrier arm is in said second extended position.

16. The needle assembly of claim 15 wherein said means for visually determining includes a color segment on said barrier arm and at least one color segment on said guide element.

17. A needle assembly having a single-handedly activatable needle barrier comprising:

a needle cannula having a proximal end, a distal end, and a lumen therethrough defining a longitudinal axis;

a needle hub having an interior cavity terminating at an open proximal end of said hub, said hub connected to said needle cannula so that said lumen is in fluid communication with said interior cavity;

a guide element connected to said needle hub having a retaining groove therethrough;

an elongate barrier arm having a proximal end and a distal end, said distal end of said barrier arm including a barrier element having a distal end, a proximal end and a needle passageway therethrough defining a barrier element longitudinal axis, said barrier arm positioned within said groove of said guide element and said needle cannula positioned at least partially within said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position, said locking means being activated by movement of said barrier arm into said second extended position, said locking means including said barrier element having a distal barrier wall with an aperture therethrough, said barrier wall aperture being effectively smaller than said needle passageway, so that when said barrier arm is in said second extended position, said distal end of said needle cannula is positioned proximally of said barrier wall and out of alignment with said barrier wall aperture;

means for releasably holding said barrier arm in said first retracted position; and finger contact surface on said barrier arm for applying digital pressure to said barrier arm to move said barrier arm into said second extended position.

18. The needle assembly of claim 17 further including an elongate needle shield having a distal end, a proximal end and a cavity therebetween for receiving said needle cannula, said proximal end of said needle shield being configured to releasably engage a portion of said guide element for holding said needle shield in a needle protecting position while said barrier arm is in said first retracted position and said needle shield being incapable of engaging said guide element when said barrier arm is in said second extended position.

19. A needle assembly having a single-handedly activatable needle barrier comprising:

a needle cannula having a proximal end, a distal end, and a lumen therethrough defining a longitudinal axis;

a needle hub having an interior cavity terminating at an open proximal end of said hub, said hub connected to said needle cannula so that said lumen is in fluid communication with said interior cavity;

a guide element connected to said needle hub having a retaining groove therethrough;

an elongate barrier arm having a proximal end and a distal end, said distal end of said barrier arm including a barrier element having a distal end, a proximal end and a needle passageway therethrough defining a barrier element longitudinal axis, said barrier arm positioned within said groove of said guide element and said needle cannula positioned at least partially within said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position, said locking means being activated by movement of said barrier arm into said second extended position, said locking means including said barrier element having a distal barrier wall with an aperture therethrough, said barrier wall aperture being effectively smaller than said needle passageway, said locking means including said distal end of said barrier arm defining a defining a distal longitudinal axis and said proximal end of said barrier arm defining a proximal longitudinal axis, said barrier arm being configured so that said distal longitudinal axis and said proximal longitudinal axis are at an obtuse angle with respect to each other and when said barrier arm is in said second extended position, said distal end of needle cannula is position proximally of said barrier wall and out of alignment with said barrier wall aperture;

means for releasably holding said barrier arm in said first retracted position; and finger contact surface on said barrier arm for applying digital pressure to said barrier arm to move said barrier arm into said second extended position.

20. The needle assembly of claim 19 further including an elongate needle shield having a distal end, a proximal end and a cavity therebetween for receiving said needle cannula, said proximal end of said needle shield being configured to releasably engage a portion of said guide element for holding said needle shield in a needle protecting position while said barrier arm is in said first retracted position and said needle shield being incapable of engaging said guide element when said barrier arm is in said second extended position.

* * * * *